United States Patent
Watanabe et al.

(10) Patent No.: US 6,815,058 B2
(45) Date of Patent: Nov. 9, 2004

(54) MEDICAL PRESSURE-SENSITIVE ADHESIVE TAPE OR SHEET, AND FIRST AID ADHESIVE TAPE

(75) Inventors: Tetsuo Watanabe, Osaka (JP); Takashi Kinoshita, Osaka (JP); Atsushi Hamada, Osaka (JP); Fumiya Shirai, Osaka (JP)

(73) Assignee: Nitto Denko Corporation, Osaka (JP)

( * ) Notice: Subject to any disclaimer, the term of this patent is extended or adjusted under 35 U.S.C. 154(b) by 0 days.

(21) Appl. No.: 09/934,578

(22) Filed: Aug. 23, 2001

(65) Prior Publication Data

US 2002/0098349 A1 Jul. 25, 2002

(30) Foreign Application Priority Data

Aug. 23, 2000 (JP) .................... P.2000-253190

(51) Int. Cl.$^7$ .................. B32B 15/04; B32B 7/12; B61F 13/00
(52) U.S. Cl. ............... 428/354; 428/343; 602/41; 602/42; 602/43; 602/44; 602/45; 602/46; 602/54
(58) Field of Search ............... 428/343, 354; 602/54, 41, 42, 43, 44, 45, 46

(56) References Cited

U.S. PATENT DOCUMENTS 5,218,033 A    6/1993  Pottick et al.
5,326,627 A  *  7/1994  Yazaki et al. ............... 428/216
6,262,330 B1 *  7/2001  Fujisawa et al. ............ 602/54

FOREIGN PATENT DOCUMENTS

EP    0 305 842 A2   3/1989
EP    1 020 196 A1   7/2000

OTHER PUBLICATIONS

JP 06016542 A English Abstract.*
XP–002233110 (May, 2000)—Abstract.
XP–002233111 (Apr., 1999)—Abstract.
XP–002233112 (Apr., 1999)—Abstract.
European Search Report dated Mar. 14, 2003.

* cited by examiner

Primary Examiner—Daniel Zirker
Assistant Examiner—Victor Chang
(74) Attorney, Agent, or Firm—Sughrue Mion, PLLC

(57) ABSTRACT

The present medical pressure-sensitive adhesive tape or sheet, comprises: a supporting base material; and an adhesive layer laminated directly or indirectly on the supporting base material, wherein the supporting base material contains: 1 to 50 parts by weight of at least one selected from the group consisting of a fatty acid, a fatty acid ester, a fatty acid amide, a higher alcohol, and a metal soap; and 100 parts by weight of at least one resin selected from the group consisting of an olefin thermoplastic elastomer, a styrene thermoplastic elastomer, and a polyester thermoplastic elastomer.

7 Claims, No Drawings

MEDICAL PRESSURE-SENSITIVE ADHESIVE TAPE OR SHEET, AND FIRST AID ADHESIVE TAPE

BACKGROUND OF THE INVENTION

1. Field of the Invention

The present invention relates to a pressure-sensitive adhesive tape or sheet for the medical treatment (i.e., medical pressure-sensitive adhesive tape or sheet; sometimes referred to as "adhesive tape or sheet for medical treatment" or "medical adhesive tape or sheet" in the present specification), and a first aid adhesive tape. More specifically, it relates to an adhesive tape or sheet for the medical treatment, and a first aid adhesive tape to be applied in the field of an attaching material for the medical use, in particular, for a roller bandage, a surgical tape, an adhesive plaster, a poultice medicine, a dressing material, an injury protecting agent, a percutaneous absorbing agent, or the like, particularly suitable for the use of those susceptible for stimulus in the skin, such as the elderly people, infants, and sickly people.

2. Description of the Related Art

As a film for the supporting base material to be used for various kinds of adhesive tapes or sheets for the medical treatment, such as a first aid adhesive tape and a surgical tape, a large number of films containing a plasticized polyvinyl chloride as the main component, produced by a calendar method or the sol cast method have been used conventionally.

The films for the supporting base material containing a plasticized polyvinyl chloride as the main component have such a characteristic that a high stress is provided in the initial stage of applying a tension, but the stress relaxation occurs suddenly according to passage of time. The stress relaxation is derives from the plasticity of the vinyl chloride film. In the case an adhesive tape (or sheet) using the film for the supporting base material having such a characteristic is attached on the skin, the tensile stress is alleviated gradually after the attachment, and consequently the burden on the skin is reduced. By using the film for the supporting base material containing the plasticized polyvinyl chloride as the main component, the attaching operativity can be ensured owing to the appropriate stress at the time of attachment as well as the feeling of being pulled can be eliminated by the stress relaxation thereafter so that the physical skin stimulus can be alleviated. Accordingly, both operativity and low stimulus can be ensured.

However, in the case the plasticized polyvinyl chloride is used, since a large amount of a plasticizer is contained, the plasticizer moves from the film to an adhesive layer, and as a result, deterioration of the pressure-sensitive adhesion force and deterioration of the aggregation force are brought about. Therefore, it is disadvantageous in that the pressure-sensitive adhesive is denatured, the vicinity of the attachment part is fouled due to flow of the pressure-sensitive adhesive, or the like.

Moreover, since the film contains a chlorine, a countermeasure for the post treatment thereof is required for recently in view of the environmental issue.

Therefore, development of flexible thermoplastic resins with a stretchability as a substitute material for the vinyl chloride has actively been promoted not only for the application in the medical field. Various thermoplastic resins such as olefin based resins, ethylene vinyl acetate copolymer based resins, and elastomer based resins have been provided as commercial products.

Specifically, for example, an ethylene methacrylate (EMA) based resin, an amorphous polyalpha olefin based resin, an ethylene vinyl acetate copolymer (EVA) based resin, anolefin based EMA blended product, a polyurethane based resin, a low density polyethylene (LDPE), a linear low density polyethylene (LLDPE) based resin, an ethylene-methylmethacrylate copolymer (EMMA) based resin, or the like, can be presented. In particular, a thermoplastic elastomer resin as an elastic non-chlorine based material has been discussed actively as a prospective material for achieving the above-mentioned object.

As the thermoplastic elastomer resin, for example, first a styrene based thermoplastic elastomer such as a styrene-butadiene-styrene block polymer has been developed. Thereafter, a vinyl chloride based elastomer (TPBC), an olefin based thermoplastic elastomer, an ester based chlorinated plastic based thermoplastic elastomer, or the like have been developed. In particular, the olefin based thermoplastic elastomer is closest to the polyvinyl chloride in terms of the weather resistance, and the cost.

Moreover, the olefin based thermoplastic elastomer improved so as to be hardly flawed has been developed recently. Examples thereof include a polypropylene based alloy with a novel highly blended type hydrogenated styrene butadiene rubber blended.

However, among these various kinds of resins, which can be presented as a substitute for the vinyl chloride resin, only a part of the thermoplastic elastomers are used for a limited area in the medical application, such as an infusion bag, a waste liquid bag for the artificial dialysis, and an infusion tube.

In contrast, application of a soft olefin such as the amorphous polyalpha olefin based resin to the film for the supporting base material is attempted as a substitute film for a polyvinyl chloride resin. However, it is not optimum in terms of the following points.

That is, since it has a low stress with respect to the tension or stretch of any strength, a problem is involved in that the operativity at the time of attachment is extremely poor at the site of medical treatment, or in contrast, a tension is always applied on the skin during the attachment operation due to too high a stress at the time of deformation so that a strong physical stimulus is applied.

Accordingly, the contradicting natures of the operativity at the time of attachment and the skin stimulus cannot be satisfied sufficiently merely by using a conventional dechlorinated vinyl based resin as it is as the film for a supporting base material of an adhesive tape (sheet) for the medical treatment.

From this viewpoint, a large number of those produced by improving a thermoplastic elastomer, which has conventionally been a material for the industrial application, have been proposed as a film for the supporting base material of an adhesive tape for the medical treatment having the same stress relaxation property as that of the vinyl chloride based resin as follows.

The conventional olefin based thermoplastic elastomers are mainly blend based thermoplastic elastomers including a polypropylene (PP) as the hard segment and an ethylene propylene rubber (EPR) as the soft segment. According to the PP/EPR as a common simple blended product, it is poorer than the chlorine based thermoplastic elastomer in terms of the compression set. Therefore, a dynamic cross-linked olefin based thermoplastic elastomer with the compression set improved by slightly dispersing the EPR in the PP while being cross-linked at the time of blending the PP/EPR has been discussed as a substitute resin for the polyvinyl chloride resin.

As the olefin based thermoplastic elastomers to be produced directly in the polymerization stage, for example, an FPO (flexible polyolefins) by Rexene Corp., a catalloy resin by Montell Polyolefins Corp., and a P.E.R. resin by Tokuyama Soda Corp. can be presented.

The catalloy resin is a resin produced by alloying an olefin based resin with an ethylene propylene rubber in the polymerization stage. Compared with the other soft resins (such as a PVC and a PE based resin), it has the excellent characteristics in terms of the heat resistance, and the tearing and piercing strengths. This can be obtained by a polymerization process technique, which has enabled alloying of polyolefins in a polymerization reactor. That is, in gas phase polymerization reactors of a large number of stages, wherein a polymerizing operation is executed each independently such that a polymer obtained in each reactor is taken out as a final product in an alloyed stage. According to this method, a synthetic rubber (ethylene propylene rubber) is blended in a polymerization stage so as to obtain a product with a far higher rubber content compared with a blended product by an extruder, or the like. In such a resin, a phase structure with an EPR phase forming a three-dimensionally continuous matrix, and a PP crystal lamella dispersed therein is provided. As a result, a high elasticity of the polyolefin and a flexibility of the rubber can be related closely, and thus a high initial elastic force and a quick stress relaxation property can be provided.

Moreover, as amorphous or low crystalline olefin based resins, an APAO resin and a CAP resin produced by Ube Industries, Ltd. can be presented. These resins are superior to the conventional olefin based resins in terms of the flexibility and the heat resistance, and furthermore, have a relatively good stress relaxation property.

However, even in the case of using the catalloy resins or the amorphous polyalpha olefin based resins, the stress relaxation property is insufficient, that is, the relaxation tendency becomes extremely dull after a certain degree of relaxation so that softening by the stress relaxation is limited. In particular, even if a small load on the skin, if it remains continuously, depending on the user, it can be recognized as an explicit skin stimulus.

Furthermore, due to poor feeling thereof, in the case they are used for an adhesive tape for the medical treatment of a first aid adhesive tape, the external appearance is poor.

SUMMARY OF THE INVENTION

In view of the problems of the technique of the related art, the present invention has been achieved, and an object thereof is to provide an adhesive tape (or a sheet) for the medical treatment and a first aid adhesive tape suitable for attaching on a bending part by using a supporting base material having appropriate flexibility and stress relaxation property as well as a good feeling as a substitute for a polyvinyl chloride film for a supporting base material.

In order to solve the problems, as a result of an elaborate discussion, the present inventors have found out that the problems can be solved by obtaining a base material with a thermoplastic elastomer such as an olefin based thermoplastic elastomer as the base polymer or a part of the base polymer, and containing an appropriate amount of various kinds of additives, which are considered to improve the flowability of a resin so as to complete the invention.

DETAILED DESCRIPTION OF THE INVENTION

An adhesive tape or sheet for the medical treatment according to the invention comprises an adhesive layer laminated directly or indirectly on a supporting base material, wherein 1 to 50 parts by weight of at least one selected from the group consisting of a fatty acid, a fatty acid ester, a fatty acid amide, a higher alcohol, and a metal soap is contained with respect to 100 parts by weight of at least one resin selected from the group consisting of an olefin based thermoplastic elastomer, a styrene based thermoplastic elastomer, and a polyester based thermoplastic elastomer.

That is, an adhesive tape or sheet for the medical treatment (hereinafter sometimes referred to as an "adhesive tape for the medical treatment" or "medical adhesive tape") according to the invention comprises an adhesive layer laminated directly or indirectly on a supporting base material, wherein 1 to 50 parts by weight of one or two or more selected from the group consisting of a fatty acid, a fatty acid ester, a fatty acid amide, a higher alcohol, and a metal soap is contained with respect to 100 parts by weight of one or two or more resins selected from the group consisting of an olefin based thermoplastic elastomer, a styrene based thermoplastic elastomer, and a polyester based thermoplastic elastomer. The adhesive tape or sheet according to the invention includes the concept of both sheet-like material of a wide width and tape-like material of a narrow width.

An olefin based thermoplastic elastomer, a styrene based thermoplastic elastomer, or a polyester based thermoplastic elastomer to be used in the invention are not particularly limited as long as the effects of the invention can be achieved, but those comprising an amorphous portion in a macro and even state by a large amount can be selected preferably.

As the olefin based thermoplastic elastomer (TPO), for example, a polypropylene based resin such as a random polypropylene, a polyethylene/butylene crystalline polyolefin, an ethylene-propylene based rubber (EPDM, EPM), an ethylene-1-butylene rubber, an ethylene-vinyl acetate copolymer, an amorphous polyα-olefin, or the like can be presented, and one selected therefrom or a polymer alloy of two or more can be used. Moreover, although a partially cross-linked product of these resins can also be used, since a total cross-linked product may deteriorate the stress relaxation property, it is not preferable in some cases. Herein, the "polymer alloy" is a concept including a simple blended product (the same is applied to the case of the following SBC). These TPO can be used in the state blended or alloyed with another thermoplastic resin. Those prepared by blending or alloying with another thermoplastic resin can also be used as a TPO as it is.

Furthermore, as the styrene based thermoplastic elastomer, a styrene-butadiene block copolymer (SBS), a styrene-isoprene-styrene block copolymer (SIS), a styrene-ethylene-styrene block copolymer (SES), a styrene-ethylene/butylene-styrene block copolymer (SEBS), and a styrene-ethylene/propylene-styrene block copolymer (SEPS), a hydrogenated styrene-butadiene rubber (HSBR) or a maleinated product thereof can be presented, and one selected therefrom or a polymer alloy of two or more can be used. Similar to the TPO, these can be used in the state blended or alloyed with another thermoplastic resin.

Among these thermoplastic elastomers, a polypropylene based resin, a polymer alloy of a polypropylene based resin and another thermoplastic elastomer resin, and a copolymer of a polypropylene based resin and other thermoplastic elastomer resin are preferable.

Furthermore, in the invention, in the case a polymer alloy of a polypropylene based resin and a thermoplastic elastomer, or a copolymer of a polypropylene based resin and a thermoplastic elastomer are used, it is particularly preferable to use an amorphous or low crystalline polyolefin based resin (propylene based polyolefin). Accordingly, by using a polyolefin based resin with the ratio of the crystalline portion in the resin drastically reduced with respect to the conventional polypropylene based resins, the stress relaxation property and the flexibility can further be improved. It is considered that the effect of improving the stress relaxation property by the fatty acid, the fatty acid ester, the fatty acid amide, the higher alcohol, and the metal soap can be performed with the multiplier effect together with the improvement of the flowability of the amorphous portion.

At the time, it is preferable to include the polyolefin based resin providing the amorphous portion (it can be low crystalline) in the thermoplastic elastomer comprising the supporting base material by 30 to 80% by weight. In the case the amorphous portion is contained by less than 30% by weight, the flexibility of the obtained supporting base material can be insufficient. In contrast, in the case it is contained by more than 85% by weight, due to too high a flexibility, the handling property and the operativity as the supporting base material can be unsatisfactory.

The ratio of the amorphous or low crystalline thermoplastic resin is set preferably 30% by weight or more, further preferably 50% by weight with respect to the total weight of the materials comprising the film for the supporting base material. In the case it is contained by less than 30% by weight, it is difficult to obtain the expected stress relaxation property and flexibility.

As a specific method for producing the amorphous or low crystalline polyolefin based resin, several methods have been proposed. For example, the method disclosed in JP-A-4-224809 can be presented. Therein, spherical titanium supporting catalyst having a 15 μm average particle size, prepared by co-pulverizing a titanium trioxide and a magnesium chloride, treated with an orthotitanic acid n-butyl, a 2-ethyl-1-hexanol, a p-toluic acid ethyl, a silicon tetrachloride, a diisobutyl phthalate, or the like is used. As an aluminum compound, an alkyl aluminum such as a triethyl aluminum is used. Furthermore, a silicon compound, in particular, a diphenyl dimethoxy silane is added as an electron donor in a polymerization vessel, and further, an ethyl iodide is added.

According to the invention, in order to optionally adjust the elastic modules, the stretchability, or the like of the amorphous or low crystalline polyolefin based resins, a crystalline polypropylene based resin can be blended or copolymerized therewith.

Moreover, according to the invention, as the amorphous or low crystalline polyolefin based resin and/or the crystalline polypropylene based resin, denatures one can be used as well. As the denatured resin, for example, those prepared by denaturing the amorphous or low crystalline polyolefin or crystalline polypropylene by, for example, an unsaturated carboxylic acid such as an acrylic acid, a methacrylic acid, an ethacrylic acid, a maleic acid, a fumaric acid, and an itaconic acid, and/or an ester, an acid anhydride, a metal salt, a derivative thereof, or the like, can be used.

Furthermore, in the case the amorphous or low crystalline polyolefin based resins and the crystalline polypropylene based resin are blended or alloyed, it is adjusted such that the amorphous or low crystalline polyolefin based resin is contained by 30 to 100% by weight, preferably 50 to 100% by weight. With a less than 30% by weight amorphous or low crystalline polyolefin based resin content, since the film for the supporting base material to be obtained has an yield point, it is not preferable for the application of the invention.

In the supporting base material to be used for the adhesive tape for the medical treatment according to the invention, one or two or more selected from the group consisting of a fatty acid, a fatty acid ester, a fatty acid amide, a higher alcohol, and a metal soap is contained. The fatty acid, or the like is contained by 1 to 50 parts by weight, preferably by 5 to 40 parts by weight with respect to 100 parts by weight of the olefin based thermoplastic elastomer and/or the styrene based thermoplastic elastomer and/or the polyester based thermoplastic elastomer.

As the fatty acid, or the like, those commonly recognized to have the effect of improving the flowability among resins, having a relatively high molecular weight can be used preferably in view of reduction of bleeding thereof. For example, esters of a branched alcohol having 14 to 18 carbon atoms and a monobasic acid or a polybasic acid such as an isostearyl laurate, an isocetyl myristate, an octyldodecyl myristate, an isostearyl palmitate, an octyldodecyl oleate, a diisostearyl adipate, a diisocetyl sebacate, a trioleyl oleate, a triisocetyl trimelliate, sorbitan trioleate, glycerin tricaprylate, and/or esters of a tetravaleic alcohol and an unsaturated fatty acid having 14 to 18 carbon atoms or a branching acid, or the like, can be presented.

Examples of the fatty acid include a palmitic acid, a stearic acid, a behenic acid, and a hydroxy stearic acid.

Examples of the fatty acid ester include a glycerol fatty acid ester, a sorbitan fatty acid ester, a polyglycerol fatty acid ester, a propylene glycol fatty acid ester, and a higher alcohol fatty acid ester.

Examples of the metal soap include a calcium stearate, a zinc stearate, a magnesium stearate, and an aluminum stearate.

Examples of the fatty acid amide include lauryl amide, tridecyl amide and stearyl amide.

Examples of the higher alcohol include lauryl alcohol, cetyl alcohol, steary alcohol, isostearyl alcohol and olein alcohol.

The supporting base material can be obtained by containing the thermoplastic elastomer and the fatty acid, or the like. Various kinds of additives and fillers can be added optionally to the mixture. For example, as the additives, a heat resistance stabilizer, an antioxidant, alight stabilizer, a electrification preventing agent, a smoothing agent, a core agent, a flame retarder, a pigment or a dye can be presented. As the filler, various kinds of inorganic or organic fillers such as a calcium carbonate, a calcium sulfate, a titanium oxide, a barium sulfate, a magnesium hydroxide, clay, or the like, can be presented.

In particular, in order to improve the stability with respect to the troubles derived from heat, the oxygen in the air, and a light beam, it is particularly preferable to add a carbon black, a 2,2-thio-bis(4-methyl-6-t-butyl phenol), dilauryl thiodipropyonate and other various known amine stabilizers and phenol stabilizers.

Moreover, by using various kinds of polymer based compatibility agents and resin improving agents in the mixture, not only the compatibility among the resins can be improved but also deterioration of the shock resistance, the drawability, the flexibility, the transparency, or the like of the obtained supporting base material can be prevented.

As the resin improving agents (or compatibility agents), specifically, a hydrogenated styrene-butadiene rubber (HSBR) or a maleinate product thereof, an ethylene-ethyl acrylate copolymer, an ethylene-acrylate-maleic anhydride copolymer, an ethylene-glycidyl methacrylate ester copolymer, a maleic anhydride grafted polypropylene, a maleic anhydride grafted ethylene polypropylene rubber, an acrylic acid grafted polypropylene, an ethylene-vinyl acetate copolymer, an ethylene-vinyl acetate/ethylene-propylene-diene/polyolefin based grafted copolymer, a metal salt of an ethylene-methacrylic acid copolymer, a chlorinated paraffin, or the like, can be presented.

These resin improving agents or the compatibility agents can be added, in general by 0.1 to 40% by weight, more preferably by 2 to 30% by weight with respect to the total amount of the resin composition for forming the supporting base film. If it is less than 0.1% by weight, either of the supporting base film forming property, the drawability, the transparency and the flexibility is remarkably deteriorated. In contrast, if it is more than 40% by weight, deterioration of the heat resistance of the obtained film, or the operativity as the supporting base material, and the blocking resistance is observed explicitly. In the case a polar group containing ethylene copolymer as the compatibility agent is added in the addition tolerance range, the heat resistance inherent to the polypropylene was not deteriorated, and even in the case it is heated at 120 to 130° C. for more than 30 minutes, denaturing thereof such as shrinkage, deformation, discoloration, or the like was not observed.

The supporting base material may further contain as a non-cross-linked rubber based polymer, at least one selected from the group consisting of an isoprene rubber, a butadiene rubber, a 1,2-polybutadiene, a styrene-butadiene rubber, a chloroprene rubber, a nitrile rubber, a butyl rubber, an isoprene-propylene rubber, a chlorosulfonated polyethylene, an acrylic rubber, an epichlorhydrine rubber, a polysulfide rubber, a silicone rubber, a methyl vinyl silicone rubber, a fluoride silicone rubber, a fluorine rubber, a urethane rubber, an acrylonitrile-butadiene rubber, a polyoxy propylene, a poly(oxy tetramethylene) glycol, a polyolefin glycol, a poly-ε-caprolactone, a polysulfide rubber, a polyisobutylene, and a polyisobutene.

The supporting base material is formed by mixing the components. The adjustment method is not particularly limited. By using conventionally known various kneaders, such as various kinds of kneaders including a kneader, a banbary mixer, and a roll, or a one axis or two axes extruder, or the like for heating, melting and kneading, the materials are formed temporarily into, in general, pellets or lumps.

The resin pellets or lumps are processed into a film-like shape. The film formation method is not particularly limited, and it is formed into a predetermined thickness by conventionally known methods such as a T die method, an inflation method, a calendar method, and a rolling method. Furthermore, a drawing process such as a vertical one axis drawing process and/or a lateral one axis drawing process can be applied thereafter. Moreover, an annealing process can be applied as needed. Of course, a throughout production is also possible by processing into a film-like shape immediately after kneading the resin composition without forming resin pellets.

Moreover, according to the invention, it is further preferable that the fatty acid or the fatty acid ester, the fatty acid amide, the higher alcohol, and the metal soap are absorbed in the film for the supporting base material from the outside by impregnation according to a method of applying, soaking or including in an adhesive, or the like after formation of the film for the supporting base material. Thereby, the fatty acid, or the like, capable of providing the resin flowability effect can be permeated selectively in the amorphous portion and the vicinity thereof so that excessive softening of the entirety of the film or bleeding can be prevented. Accordingly, the stress relaxation property can effectively be improved specifically.

The thickness of the supporting base film is not particularly limited, and it can be set optionally according to the purpose of use. In general, it is formed in a range of about 2 to 1,000 μm. If it is less than 2 μm, the elasticity can be insufficient, or the handling operation is disturbed. In contrast, if it is more than 1,000 μm, the flexibility is unsatisfactory.

At the time, the grade, composition ratio, film thickness, or the like are adjusted such that the tensile stress immediately after a stretching operation for 10% in the longitudinal direction by a 300 mm/min rate with a 20 mm inter-chuck distance of a tensile tester, and a 20 mm sample width is in a range of 200 to 2,500 $gf/mm^2$, preferably 300 to 1,600 $gf/mm^2$. If the tensile stress is less than 200 $gf/mm^2$, for example, at the time of attaching a roller bandage, the supporting member is stretched out so that the advantageous characteristics of the invention, such as the operativity at the time of attachment, the feeling, and further, the fixing property on the skin of an infusion tube, or the like, are deteriorated. In contrast, if it is more than 2,500 $gf/mm^2$, the flexibility is lacked so that the closely fixing property at the time of attachment on the skin, the followability to the skin, the feeling, or the like are lowered. The "longitudinal direction" here denotes the direction to which the tension can easily be applied, such as the winding direction in the case of the roller bandage, and in general, the longer axis direction in the case of the adhesive plaster. However, in the case the tension can be applied in the four direction, such as in a dressing material for the medical treatment, it is not limited to one direction.

Moreover, in the supporting base material in the adhesive tape (sheet) for the medical treatment according to the invention, the supporting base film can be used not only in a single layer but also in the state processed into a laminated member as a laminated film as needed in order to provide various characteristics. As the films to be laminated, it is not limited to the supporting base film, but the other various plastic films, non-woven fabrics, porous films, or the like can be presented. Furthermore, in the case of the lamination, it is not limited to the simple lamination of the supporting base film, but it is preferable to laminate the other films, or the like alternately. At the time, it is preferable to expose a film, or the like other than the supporting base film on one side or both sides.

Accordingly, by laminating a film of different material on the supporting base film, functions of providing (improving) the anchoring property, providing the anti-blocking property, the bleeding prevention for the adhesive component, or the like can be achieved. It is preferable to adjust the thickness of the film and the number of the lamination so as to effectively provide the effects. Moreover, the fatty acid, the fatty acid ester, or the like can be included in any layer of the laminated base material.

At the time, it is preferable to adjust such that the stress relaxation ratio as the supporting base material is 60% or less. By accordingly having the 60% or less stress relaxation ratio, the feeling of being pulled after attachment can be eliminated. Furthermore, in consideration of a stimulus-sensitive person, it is preferable to set the stress relaxation ratio at 40% or less.

According to an adhesive sheet for the medical treatment, or the like of the invention, an adhesive layer is formed on one side or both sides of the supporting base material accordingly obtained.

The adhesive to be use din the adhesive layer is not particularly limited, and it can be one used in an ordinary adhesive sheet for the medical treatment. That is, one or two or more from appropriate adhesives such as an acrylic based adhesive, a rubber based adhesive, and a silicone based adhesive, can be used.

Particularly in consideration of the stimulus on the skin, it is preferable to use the acrylic based adhesive. Moreover, in the case the acrylic based adhesive is used in the supporting base material according to the invention, the stress relaxation property can further be improved.

These adhesives can be applied on the supporting base material by a conventionally known method so as to form an adhesive layer. At the time, the thickness of the adhesive layer is not particularly limited, and it can be formed by about 10 to 200 μm, preferably 20 to 100 μm.

Furthermore, a first aid adhesive tape according to the invention comprises a liquid absorbent pad provided in the central area of the adhesive layer surface formed on one side of the supporting base material. As the liquid absorbent pad, those conventionally known can be used. For example, a gauze, a woven-fabric, a non-woven fabric, a composite product of an absorbent cotton and a non-woven fabric, a composite product of an absorbent cotton and a knitted net, or the like, can be presented.

Moreover, although the size thereof differs depending upon the size of an adhesive tape for the medical treatment, or the like, it is preferable to adjust the size such that the adhesive layer of the adhesive tape is exposed by at least about 2 to 3 mm around the liquid absorbent pad.

According to the first aid adhesive tape according to the invention, it is preferable to cover the adhesive layer surface with a separator until use in order to prevent fouling of the adhesive layer surface. In this case, as the separator to be used, it is preferable to use one including a silicone based releasing agent containing an organosiloxane based polymer in order to improve the releasing property with respect to the adhesive layer.

EXAMPLE

Examples of adhesive sheets for the medical treatment were produced, using various supporting base materials for confirming the effects of the invention. It is needless to say that the invention is not limited to the following examples. Hereafter, "%" denotes the "% by weight", and the "part" denotes the "part by weight".

[Production of the Supporting Base Material]

Total 9 kinds of materials including a homopolypropylene (homo PP) (product name "grand polymer", E101P, produced by Grand Polymer Corp.), a low density polyethylene (LDPE) (product name "Petresene", 339, produced by Toso Corp.), an ethylene-vinyl acetate copolymer (EVA) (product name "Evatate", D2010F, produced by Sumitomo Kagaku Corp.), an ethylene propylene rubber (EPR) (product name "TSREP", EP01P, produced by Nihon Gosei Rubber Corp.), a PP/EPR copolymer (product name "Catalloy Adflex", KS-221P, Montell-JPO Corp.), an APAO/PP mixture (product name "CAP", CAP350, produced by Ube Industries, Ltd.), a styrene based thermoplastic elastomer (product name "Rabaron", SJ4460N, produced by Mitsubishi Kasei Corp.), and a polyester based thermoplastic elastomer (product name "Primalloy", A1600, produced by Mitsubishi Kasei Corp.) were used.

As the fattyacid, a stearic acid (product name "NAA-180", produced by NOF Corporation.), as the glycerol fatty acid ester, a glycerol diacetoseto monostearate (product name "PoemG-048", produced by Riken Vitamin Corp.), and as the sorbitan fatty acid ester, a trioleic acid fatty acid ester (product name "Emasol SOP-30, produced by Kao Corp.) were used. Moreover, as the fatty acid amide, an N,N'-distearyl adipic acid amaid (product name "Sparix XSA", produced by Nihon Kasei Corp.), as the higher alcohol, a stearyl alcohol (product name "Karcol 86", produced by Kao Corp.), as the metal soap, a magnesium stearate (product name "magnesium stearate", produced by NOF Corporation.) were used respectively. They are described as a resin flowability agent in the tables.

Moreover, as the resin improving agent (compatibility agent), an ethylene-acrylic acid ester-maleic anhydride copolymer (product name "Bondain", AX-8390, produced by Atokem Corp.), a solution polymerization styrene butadiene rubber hydrogenated product (product name "DYNARON", CEBC6200P, produced by Nihon Gosei Rubber Corp.), and an acrylic rubber (product name "Leo Coat H-624", produced by Dai Ichi Lace Corp.) were used.

As comparative examples, those without adding a fatty acid, a metal soap, and a resin improving agent were used.

With the thermoplastic resins, the fatty acid, or the like, and the resin improving agents (compatibility agents), supporting base films of the examples 1 to 14 and the comparative examples 1 to 10 were produced according to the composition ratios shown in the tables 1 to 4.

Moreover, as to the supporting base film, using a 201 pressuring kneader, a base polymer (thermoplastic resin) was introduced after heating to a 125° C. can member temperature, and was kneaded while gradually heating the can member until the can member temperature becomes 170° C. After raising the temperature to 170° C., as needed, a resin improving agent (compatibility agent) was introduced, and the kneading operation was continued for further 30 minutes. Finally, a fatty acid, a fatty acid ester, a fatty acid amide, a higher alcohol, and a metal soap were introduced, and the kneading operation was continued for further 30 minutes. Thereafter, as needed, resin pellets were produced.

Then, with the resin composition (lumps or resin pellets), the supporting base films of the examples 9, 10 and the comparative example 8 shown in the table 3 were produced by the following extrusion shaping method, and the other supporting base films were produced by the rolling shaping method.

(Rolling Shaping Method)

With a compression shaping machine, the resin compositions (resin lumps) were pressed for about 15 minutes with a 150 to 220° C. heating temperature, and a 40 to 80 kgf/cm$^2$ pressure condition. At the time, the heating temperature and the pressure were adjusted such that the obtained film thickness can be 80 to 100 μm.

(Extrusion Shaping Method, T Die Method)

A two axes extrusion drawing machine (T die gap length: 120 mm, gap width: 1 mm) was used. The extruder cylinder temperature was adjusted between 150 to 220° C. optionally according to the kind of the resin. The resin compositions were mixed in a cylinder, and cooled down by a cooling roll while being extruded from a T die. Furthermore, the drawing film formation was carried out such that the film thickness can be about 80 μm by optionally adjusting the rotation ratio of the two drawing rolls. Moreover, after the drawing and film formation, after passing through the cooling roll again, the film was wound up.

However, in the case of the example 9, the resin flowability agent was not contained in the resin pellets but was mixed during the kneading operation for the film formation. Moreover, in the case of the example 10, the resin flowability agent was applied evenly on the film surface after the film formation and was left at 60° C. for 5 days so as to permeate and impregnate in the film. At the time, the film surface was wiped off with an ethanol after the permeation, and the remained film weight was measured. The weight difference was calculated with respect to the film before the permeation so as to calculate the permeated and impregnated fatty acid ester, the fatty acid amide, or the like. In the tables, the impregnation amount is shown.

[Production of the Adhesive Sheet for the Medical Treatment]

With the supporting base films of the examples 6, 9, and the comparative example 6 obtained as mentioned above used as a supporting base material in a single layer, an acrylic based resin (composition weight ratio 5:95) made of an acrylic acid and an acrylic acid isooctyl ester on one side thereof was applied so as to have a 40 μm adhesive layer thickness so as to obtain the adhesive sheets for the medical treatment of the examples and the comparative examples.

[Production of the First Aid Adhesive Tape]

With the supporting base films of the examples 11 to 14, and the comparative example 7 obtained as mentioned above used as the supporting base material in a single layer, an acrylic based resin (composition weight ratio 5:95) made of an acrylic acid and an acrylic acid isooctyl ester on one side thereof was applied so as to have a 40 μm adhesive layer thickness so as to obtain adhesive sheets for the medical treatment. The adhesive sheets for the medical treatment were cut into a 19 mm×72 mm size, and a gauze pad of a 12 mm×20 mm size was provided in the central area of the adhesive layer surface so as to obtain the first aid adhesive tapes according to the examples and the comparative examples.

[Evaluation Test for the Supporting Base Material]

With the various supporting base films obtained as mentioned above, the following evaluation test was executed. As test samples, each of the films were cut into a 20 mm width and a 20 mm length size, and were used. Moreover, with a tensile tester (Autograph AGS-100D, produced by Shimadzu Corporation.), it was measured under a 23° C. room temperature, and 65% RH humidity condition. Furthermore, prior to the measurement, the test samples were left for more than 30 minutes in the same condition. Results are shown in the tables 1 to 4.

(Initial Stress)

With the tensile tester, the samples were drawn by a 500 mm/min tensile rate so as to measure the change of the tensile stress values for finding the stretch-stress curve. From the stretch-stress curve, the tensile stress (modulus, unit gf/20 mm) in the tensile initial stage was found.

(Stretching Ratio at the Time of Rupture)

With the same test condition, the tensile test was executed, and the stretching ratio (%) was measured when the test samples were ruptured.

(Elastic Modules)

With the same test condition, the tensile test was executed, and the inclination (gf/mm$^2$) of the straight line linking the two points of the 0 m stretch and 2 mm stretch was found from the stretch-stress curve.

(Stress Relaxation Ratio)

With the tensile tester, the samples were drawn by a 500 mm/min tensile rate to a 10% stretching ratio so as to measure the change of the tensile stress value by passage of time. By the following formula, the stress relaxation ratio (%) was calculated.

Stress relaxation ratio (%)=(tensile stress after 5 minutes/initial tensile stress)×100

The "initial tensile stress" denotes the maximum tensile stress value from immediately after starting the tension operation to the 10% stretch.

(Stress Half Life Time)

With the tensile tester, the samples were drawn by a 500 mm/min tensile rate to a 10% stretching ratio so as to measure the change of the tensile stress value by passage of time, and the stress relaxation curve was found. Thereafter, the time needed for having the initial tensile stress to half was found from the stress relaxation curve. The tension start time was defined to be 0 hour. [Evaluation Test for the Adhesive Sheet for the Medical Treatment]

The adhesive sheets for the medical treatment of the examples and the comparative examples were each cut into a 5 cm×5 cm (25 cm$^2$) size so as to obtain samples for attaching on the skin. The obtained samples for attaching on the skin were attached on the inner side of the arm (portion susceptible for inflammation), and the elbow (bending portion) of 12 healthy people for 4 hours for the evaluation by 5 grades as shown in the table 5 for the attaching feeling, the skin bonding property, and the skin stimulus. Results are shown in the table 5.

[Evaluation Test for the First Aid Adhesive Tape]

With the first aid adhesive tapes of the examples and the comparative examples attached and wound around by a wrapping film on the second joint of the second finger of 12 healthy people, they led an ordinary life for 8 hours for the evaluation by 5 grades as shown in the table 6 for the attaching feeling, the skin bonding property, and the skin stimulus. Results are shown in the table 6.

[Test Results]

As it is observed in the tables 1 to 4, according to the films for the supporting base material of the examples, it was confirmed that the object of the invention can be achieved by lowering stress relaxation ratio as well as by remarkably lowering the stress half life time without drastically increasing the initial stress.

Moreover, as it is observed in the tables 5 and 6, according to the adhesive sheets for the medical treatment and the first aid adhesive tapes of the examples of the invention, better evaluation can be obtained in all of the attaching feeling, the skin bonding property, and the skin stimulus with respect to those of the comparative examples.

TABLE 1

| | Base polymer | Mixing amount (part) | Resin flowability agent | Mixing amount (part) | Resin improving agent, compatibility agent | Mixing amount (part) | Stretching ratio at the time of rupture (%) | Initial stress (gf/20 mm) | Stress relaxation ratio (%) | Stress half life time (second) |
|---|---|---|---|---|---|---|---|---|---|---|
| Comparative Example 1 | LDPE + EVA (Blending ratio: 1:1) | 100 | — | — | — | — | 768 | 890 | 74 | 500< |
| Comparative Example 2 | LDPE + EVA (Blending ratio: 1:1) | 100 | Poem G-048 | 20 | — | — | 610 | 750 | 51 | 500< |
| Comparative Example 3 | homo PP | 100 | — | — | Bondain AX8390 | 20 | 108 | 3725 | 53 | 285 |
| Comparative Example 4 | homo PP | 100 | Emasol SOP-30 | 22 | Bondain AX8390 | 20 | 120 | 3210 | 45 | 222 |
| Comparative Example 5 | homo PP + EPR (Blending ratio: 1:1) | 100 | — | — | Bondain AX8390 | 20 | 210 | 1162 | 49 | 135 |
| Example 1 | homo PP + EPR (Blending ratio: 1:1) | 100 | Emasol SOP-30 | 20 | Bondain AX8390 | 20 | 42 | 1080 | 35 | 44 |
| Example 2 | homo PP + EPR (Blending ratio: 1:1) | 100 | Karcol 86 | 15 | Bondain AX8390 | 20 | 80 | 1568 | 32 | 50 |

TABLE 2

| | Base polymer | Mixing amount (part) | Resin flowability agent | Mixing amount (part) | Resin improving agent, compatibility agent | Mixing amount (part) | Initial stress (gf/20 mm) | Stress relaxation ratio (%) | Stress half life time (second) |
|---|---|---|---|---|---|---|---|---|---|
| Comparative Example 3 | Catalloy KS-221P | 100 | — | — | — | — | 572 | 41 | 80 |
| Example 3 | Catalloy KS-221P | 100 | Emasol SOP-30 | 20 | — | — | 543 | 27 | 14 |
| Example 4 | Catalloy KS-221P | 100 | Emasol SOP-30 | 20 | Dynaron CEBC 6200P | 10 | 513 | 23 | 12 |
| Comparative Example 7 | CAP350 | 100 | — | — | — | — | 570 | 48 | 50 |
| Example 5 | CAP350 | 100 | Emasol SOP-30 | 10 | — | — | 540 | 25 | 12 |
| Example 6 | CAP350 | 100 | Emasol SOP-30 | 10 | Dynaron CEBC 6200P | 5 | 450 | 20 | 10 |
| Example 7 | CAP350 | 100 | Emasol SOP-30 | 10 | Leo Coat H-624 | 10 | 430 | 15 | 5 |
| Example 8 | CAP350 | 100 | Sparix ZSA | 30 | — | — | 480 | 21 | 16 |

TABLE 3

| | Base polymer | Mixing amount (part) | Resin flowability agent | Mixing amount (part) | Resin improving agent, compatibility agent | Mixing amount (part) | Elastic modulus (gf/20 mm$^2$) | Stress relaxation ratio (%) | Stress half life time (second) |
|---|---|---|---|---|---|---|---|---|---|
| Comparative Example 8 | Catalloy KS-221P | 100 | — | — | — | — | 965 | 50 | 68 |
| Example 9*1 | Catalloy KS-221P | 100 | Poem G-048 | 25 | — | — | 803 | 32 | 20 |
| Example 10*2 | Catalloy KS-221P | 100 | Poem G-048 | 18 | — | — | 955 | 25 | 12 |

*1: A resin flowability agent is added at the time of kneading the resin.
*2: A resin flowability agent is added by impregnation after the film formation.

TABLE 4

| | Base polymer | Mixing amount (part) | Resin flowability agent | Mixing amount (part) | Stretching ratio at the time of rupture (%) | Elastic modules (gf/20 mm$^2$) | Stress relaxation ratio (%) | Stress half life time (second) |
|---|---|---|---|---|---|---|---|---|
| Comparative Example 9 | Rabaron SJ4460N | 100 | — | — | 710 | 1350 | 70 | 500< |
| Example 11 | Rabaron SJ4460N | 100 | Emasol SOP-30 | 29 | 560 | 1262 | 42 | 356 |
| Comparative Example 10 | Primalloy Al600 | 100 | — | — | 780 | 1285 | 82 | 500< |
| Example 12 | Primalloy Al600 | 100 | Emasol SOP-30 | 14 | 480 | 1331 | 45 | 288 |
| Example 13 | Primalloy Al600 | 100 | NAA-180 | 10 | 600 | 1090 | 42 | 220 |
| Example 14 | Primalloy Al600 | 100 | Magnesium stearate | 20 | 580 | 1205 | 50 | 280 |

TABLE 5

| Supporting base material | Attaching feeling | | Skin bonding property | | Skin stimulus | |
|---|---|---|---|---|---|---|
| | Arm | Elbow | Arm | Elbow | Arm | Elbow |
| Example 6 | 4.8 | 4.3 | 4.7 | 4.5 | 4.5 | 4.3 |
| Example 9 | 4.9 | 4.5 | 4.4 | 4.3 | 4.6 | 4.2 |
| Comparative Example 6 | 3.7 | 3.4 | 2.5 | 3.5 | 3.0 | 3.6 |

Attaching feeling: 5 (good) - 4–3 (ordinary) - 2–1 (poor)
Skin bonding property: 5 (good) - 4–3 (ordinary) - 2–1 (poor)
Skin stimulus: 5 (good) - 4–3 (ordinary) - 2–1 (poor)

TABLE 6

| Supporting base material | Attaching feeling | Skin bonding property | Skin stimulus |
|---|---|---|---|
| Example 11 | 4.5 | 4.6 | 4.8 |
| Example 12 | 4.9 | 4.8 | 4.5 |
| Example 13 | 4.5 | 4.5 | 4.2 |
| Example 14 | 4.6 | 4.0 | 4.8 |
| Comparative Example 7 | 3.2 | 3.0 | 4.0 |

Attaching feeling: 5 (good) - 4–3 (ordinary) - 2–1 (poor)
Skin bonding property: 5 (good) - 4–3 (ordinary) - 2–1 (poor)
Skin stimulus: 5 (good) - 4–3 (ordinary) - 2–1 (poor)

According to the invention, compared with the conventional supporting base materials, which have been developed as a substitute for a vinyl chloride resin, a supporting base material to be relaxed to a low stress region in a relatively short relaxation time can be obtained. Therefore, an adhesive tape or sheet for the medical treatment having good skin bonding property and feeling can be provided with little physical stimulus to the skin even in the case of attachment over a long time.

Thereby, a roller bandage, an adhesive plaster, a first aid adhesive tape, a dressing material, a poultice medicine, a percutaneous absorbing agent, or the like for the medical treatment, using a substitute for a vinyl chloride resin film as the supporting base material can be provided widely.

Moreover, by adding a resin improving agent (compatibility agent), the blocking property and the anchoring property with respect to an adhesive can be adjusted further easily so that an adhesive sheet or tape for the medical treatment, and a first aid adhesive tape can be provided with a further better handling property and the excellent attaching property.

The entire disclosure of each and every foreign patent application from which the benefit of the foreign priority has been claimed in the present application is incorporated herein by reference, as if fully set forth herein.

What is claimed is:

1. A medical pressure-sensitive adhesive tape or sheet, which comprises: a supporting base material; and an adhesive layer laminated directly or indirectly on the supporting base material,
wherein the supporting base material contains: 1 to 50 parts by weight of at least one selected from the group consisting of a fatty acid, a fatty acid ester, a fatty acid amide, a higher alcohol, and a metal soap; and 100 parts by weight of at least one resin selected from the group consisting of an olefin thermoplastic elastomer, a styrene thermoplastic elastomer, and a polyester thermoplastic elastomer, wherein the fatty acid ester is at least one selected from the group consisting of a glycerol fatty acid ester, a sorbitan fatty acid ester, a polyglycerol fatty acid ester and a propylene glycol fatty acid ester,
with the proviso that the supporting base material does not contain a filler.

2. The medical pressure-sensitive adhesive tape or sheet according to claim 1, wherein the olefin thermoplastic elastomer is at least one selected from the group consisting of: a polypropylene resin; a polymer alloy of a polypropylene resin and a thermoplastic elastomer; and a copolymerization product of a polypropylene resin and a thermoplastic elastomer.

3. The medical pressure-sensitive adhesive tape or sheet according to claim 1, wherein the at least one selected from the group consisting of the fatty acid, the fatty acid ester, the fatty acid amide, the higher alcohol and the metal soap is applied or soaked after film formation of a base film to be the supporting base material.

4. The medical pressure-sensitive adhesive tape or sheet according to claim 1, wherein the metal soap is at least one selected from the group consisting of a calcium stearate, a zinc stearate, a magnesium stearate, and an aluminum stearate.

5. The medical pressure-sensitive adhesive tape or sheet according to claim 1, wherein the supporting base material further contains a resin improving agent.

6. The medical pressure-sensitive adhesive tape or sheet according to claim 5, wherein the resin improving agent is at least one selected from the group consisting of a hydrogenated styrene-butadiene rubber or a maleinated product thereof, an ethylene-ethyl acrylate copolymer, an ethyleneacrylate-maleic anhydride copolymer, an ethylene-glycidyl methacrylate ester copolymer, a maleic anhydride grafted polypropylene, an ethylene-vinyl acetate copolymer, an ethylene-vinyl acetate/ethylene-propylene-diene/polyolefin grafted copolymer, a metal salt of an ethylene-methacrylic acid copolymer, and a chlorinated paraffin.

7. A first aid adhesive tape comprising: a medical pressure-sensitive adhesive tape or sheet according to claim 1; and a liquid absorbent pad provided in the central area of the adhesive layer surface of the medical tape or sheet.

* * * * *